United States Patent [19]
Orr

[11] Patent Number: 5,325,883
[45] Date of Patent: Jul. 5, 1994

[54] DEVICE AND METHOD FOR CARPAL TUNNEL RELEASE

[76] Inventor: Terrence R. Orr, 2141 White Sands Dr., South Lake Tahoe, Calif. 96150

[21] Appl. No.: 13,287

[22] Filed: Feb. 4, 1993

Related U.S. Application Data

[62] Division of Ser. No. 787,029, Nov. 4, 1991, abandoned.

[51] Int. Cl.$^5$ .............................................. A61B 17/32
[52] U.S. Cl. ................................... 128/898; 606/172; 606/191
[58] Field of Search .................. 604/22, 51, 104, 164; 606/159, 170, 172, 191, 198; 128/898

[56] References Cited

U.S. PATENT DOCUMENTS

| | | |
|---|---|---|
| 4,461,280 | 7/1984 | Baumgartner . |
| 4,819,620 | 4/1989 | Okutsu . |
| 4,962,770 | 10/1990 | Agee et al. ............................ 128/898 |
| 4,963,147 | 10/1990 | Agee et al. ............................ 606/170 |
| 5,029,573 | 7/1991 | Chow . |
| 5,089,000 | 2/1992 | Agee et al. ............................ 606/170 |
| 5,179,963 | 1/1993 | Berger .............................. 606/192 X |
| 5,197,971 | 3/1993 | Bonutti ................................ 606/192 |
| 5,269,796 | 12/1993 | Miller et al. ...................... 606/170 X |

FOREIGN PATENT DOCUMENTS 2737014  3/1979  Fed. Rep. of Germany .

OTHER PUBLICATIONS

Chow, J. C. Y., "An Illustrated Guide To Endoscopic Release of the Carpal Ligament", Jun., 1991.
Chow, J. C. Y., "A Breakthrough in Carpal Tunnel Release", Dec., 1990. (Dyonics Brochure).
Chow, J. C. Y., "Endoscopic Release of the Carpal Ligament: A New Technique for Carpal Tunnel Syndrome", The Journal of Arthroscopic and Related Surgery, vol. 5(1), pp. 19-24.
Okutsu et al., "Endoscopic Management of Carpal Tunnel Syndrome", The Journal of Arthroscopic and Related Surgery vol. 5(1), pp. 11-18, 1989.
Agee, J. M., "The Agee Surgical Technique and User's Guide" 1990.
Kenneth W. E. Paine, Konstantinos S. Polyzoidis, "Carpal Tunnel Syndrome, Decompression using the Paine Retina-culotome", J. Neurosurg 59: pp. 1031-1036, 1983.
Ruggles Corporation brochure titled "Neurosurgical Instruments" 2 pp. 1984.

Primary Examiner—David Isabella
Assistant Examiner—MaryBeth O. Jones
Attorney, Agent, or Firm—W. Patrick Bengtsson; Douglas E. Denninger

[57] ABSTRACT

A device and method for treating a patient who is experiencing carpal tunnel syndrome is provided. The invention involves a cannula which has a closed blunt end and an open end. The cannula is dimensioned so that an endoscope and a knife can be simultaneously manipulated inside the cannula. A slot is provided between the ends of the cannula for viewing and incising the carpal ligament. The cannula preferably has a handle attached near its open end. The cannula is typically employed in conjunction with an endoscope and a knife to cut the patients transverse carpal ligament through a small wrist incision, thereby minimizing trauma to surrounding tissue, and post-operative recovery time.

8 Claims, 3 Drawing Sheets

5,325,883

DEVICE AND METHOD FOR CARPAL TUNNEL RELEASE

This is a divisional of co-pending application Ser. No. 07/787,029, filed on Nov. 4, 1991, now abandoned.

FIELD OF THE INVENTION

The invention relates to carpal tunnel syndrome therapy. In particular, the invention involves a device and method for cutting the transverse carpal ligament through a small volar wrist incision, while minimizing trauma to surrounding tissue and allowing rapid recovery.

BACKGROUND OF THE INVENTION

Carpal tunnel syndrome is a debilitating condition which afflicts many people. It is commonly associated with activities involving repetitive movements of the wrist and hand, and is therefore prevalent in the workforce. Associated conditions include diabetes and hypothyroidism. Conservative measures of rest, immobilization and anti-inflammatory medication are effective alternatives to surgery in approximately 50% of cases.

The syndrome is a compression neuropathy where the median nerve is compressed in the carpal tunnel. Traditionally an open surgical release of the transverse carpal ligament to decompress the median nerve has been the treatment of choice. However, this technique requires a large incision beginning one centimeter proximal to the volar wrist flexion crease, extending 5 to 6 centimeters (cm) distally. The incision is carried through the skin, subcutaneous fat, and palmar fascia in order to expose the ligament. While this technique permits constant visualization and control, it is followed by significant postoperative pain, scarring, loss of grip and pinch strength. Typical recovery time is usually 8-12 weeks.

In an effort to minimize trauma to surrounding tissue, surgeons have developed procedures for cutting the transverse carpal ligament through a small transverse entry portal near the patient's wrist utilizing endoscepic techniques.

One such technique, described by Agee et al., involves insertion of a blade assembly through a small wrist incision. "The Agee Surgical Technique and User's Guide", 3M HealthCare (1990). The assembly includes a blade which is distally located from a viewing port. Thus, with the Agee device, the surgeon cannot actually view the ligament cutting procedure. Consequently, accidents such as severance of the median nerve have occurred. Another problem with Agee's technique is that the entire cannula/blade assembly must be repeatedly moved during the procedure, thereby increasing the probability of injury to surrounding tissue or structures.

Another endoscopic technique, discussed by C. Y. Chow in "Endoscopic Release of the Carpal Ligament: A New Technique for Carpal Tunnel Syndrome", The Journal of Arthroscopic and Related Surgery, Vol. 5(1), pages 19-24 (1989), requires two incisions located on opposite sides of the transverse carpal ligament. The surgeon cuts an entry portal near the patient's wrist and an exit portal in the patient's palm. An open ended cannula is passed into the wrist portal, under the transverse carpal ligament and out the palm portal. The surgeon inserts a knife through one end of the cannula and an endoscope through the other end of the cannula. A problem with this technique is that it requires two incisions rather than one. Another problem is that the palm incision must be performed quite precisely in order to avoid severing palmar nerves and arteries. An additional problem with Chow's technique is that cutting is performed from proximal to distal edges of the ligament putting distal structures such as nerves and arteries in jeopardy.

Another endoscopic technique, disclosed by Okutsu, et al. in "Endoscopic Management of Carpal Tunnel Syndrome", The Journal of Arthroscopic and Related Surgery, Vol. 5(1), pages 11-18 (1989), involves inserting a clear plastic endoscopic sheath into a wrist incision. A hook knife is eventually used to cut the ligament while the procedure is viewed through the transparent sheath. A problem with this approach is that there is no sheath for the knife to prevent accidental cutting while moving the knife to and from the intended cutting position.

SUMMARY OF THE INVENTION

These and other problems with prior devices and procedures are solved by the present invention which includes a device for guiding a knife and an endoscope in a procedure for cutting the transverse carpal ligament. The device includes a cannula having a closed blunt end and an open end for receiving both the knife and the endoscope. The cannula has a slot extending between its ends for allowing viewing and cutting of the carpal ligament.

Another embodiment of the present invention involves a kit for performing a carpal tunnel release procedure. The kit includes a cannula, as described above, together with dilators of various diameters, an elevator, an endoscope, a hooked knife with a shaft angle of approximately 45°, and a hooked probe with a shaft angle of approximately 45°. The dilators are used to develop a pathway for passage of the cannula through a small wrist incision. The elevator is used to free bursal tissue from the deep surface of the ligament. The endoscope is inserted into the cannula and used to view the ligament through the cannula slot. The hooked probe is used to locate the distal edge of the carpal ligament prior to cutting. The knife is inserted into the cannula and is used to cut the transverse carpal ligament through the cannula slot. The cannula is dimensioned so that the endoscope and the knife can be simultaneously contained and cooperatively manipulated within the cannula.

Another embodiment of the present invention involves a method of using the cannula device. A small transverse incision is made 1 cm proximal to the volar flexion crease of the patient's wrist. A pathway through the carpal tunnel is gradually enlarged by inserting a series of dilators, thereby defining the desired location for the cannula. The bursal tissue is then freed from the deep surface of the transverse carpal ligament. The closed blunt end of the cannula is inserted into the wrist incision and under the transverse carpal ligament. Next, the ligament is viewed through an endoscope which is positioned inside the cannula. The distal margin of the ligament is identified by probing with a hooked probe. The transverse carpal ligament is then cut in a distal to proximal manner by a hooked knife which is moved within the cannula slot, thus relieving carpal tunnel compression on the median nerve.

DETAILED DESCRIPTION OF THE PREFERRED EMBODIMENTS

A carpal tunnel release procedure involves cutting the patient's transverse carpal ligament to relieve pressure on the median nerve. The traditional procedure simply requires cutting the tissue directly above the ligament until the ligament is exposed for direct visualization and cutting. While this technique is straight forward and reasonably safe, the patient's recovery time is slow and a significant scar results from the surgery.

Therefore, surgeons are now developing techniques for cutting the transverse carpal ligament through small incisions by using endoscopic techniques, thereby minimizing scarring and recovery time. Two important objectives of such an endoscopic technique are: 1) to move the knife to the desired cutting position without accidentally cutting other tissue; and 2) to allow constant visualization of the ligament while it is being cut.

In the present invention the surgeon employs a specially designed cannula having a slot extending between a closed blunt end and an open end. The cannula is first positioned under the transverse carpal ligament so that the slot tracks the desired cutting line. The cannula then functions as a sheath for guiding both an endoscope and a knife to the cutting site. The slot is large enough to simultaneously contain and allow cooperative manipulation of the endoscope and the knife so that the surgeon can continuously visualize and monitor the cutting process. Thus, the present invention allows a surgeon to cut the transverse carpal ligament through one small volar incision near the patient's wrist, while constantly visualizing the procedure.

Unlike the Agee technique which requires repeated movement of the cannula/blade assembly, in the present invention the cannula stays in a fixed position during the cutting procedure, thus avoiding potential problems due to reinsertion into different locations or neural structure injury which may occur if the blade fails to retract. Unlike the Chow technique in which the ligament is cut from proximal to distal edges, in the present invention the ligament is cut from its distal to proximal edges, thereby minimizing the possibility of severing adjacent nerves and arteries.

The following discussion refers to the Figures in order to explain refinements and details of the preferred embodiments of the present invention. Throughout the Figures the same numbers are used to refer to like structures.

Figure 1:
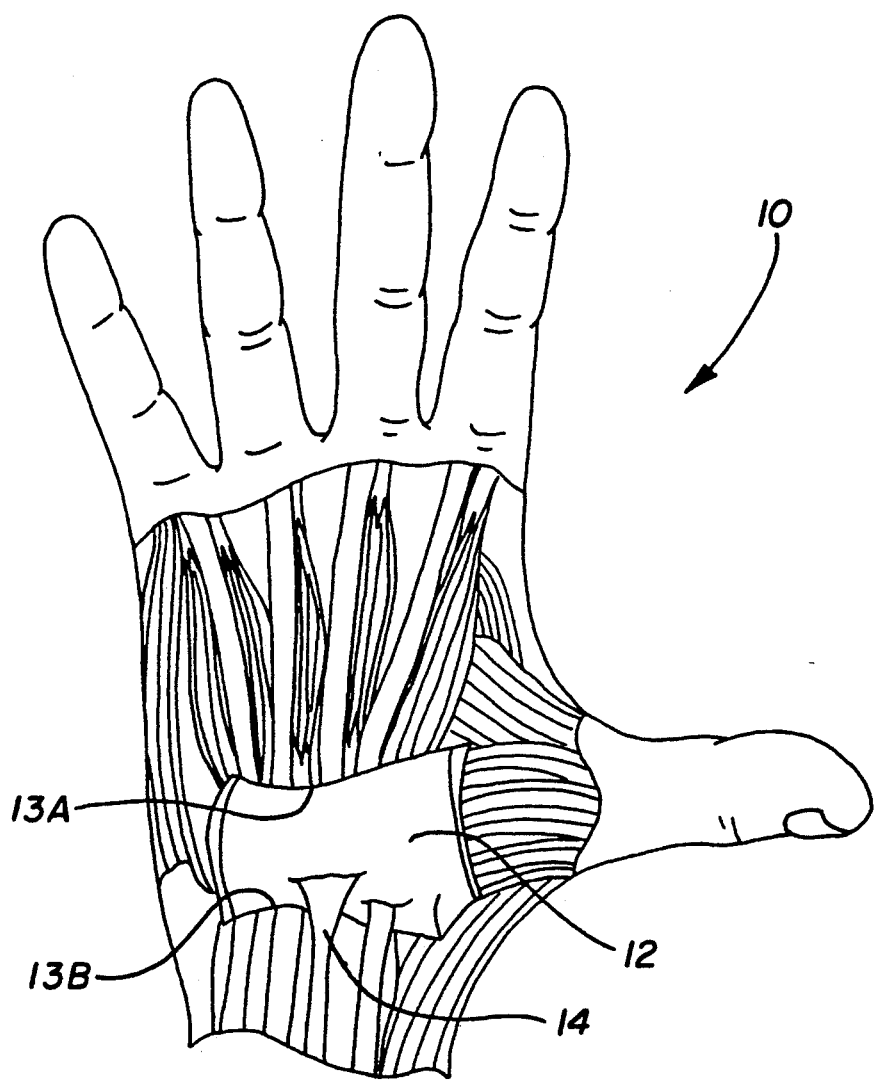
FIG. 1 is a top view of subcutaneous structures in a patient's wrist and palm which relate to the present invention.

As shown in FIG. 1, a patient's hand 10 has a transverse carpal ligament 12 which forms the roof of the "carpal tunnel." The floor and sides of the tunnel are formed by the bones of the wrist. The median nerve 14 and nine tendons pass through the carpal tunnel. Carpal tunnel syndrome results from compression exerted on the median nerve 14 by the transverse carpal ligament 12. In the present invention carpal tunnel syndrome is treated by cutting the transverse carpel ligament 12 from its distal edge 13A to its proximal edge 13B.

Figure 2:
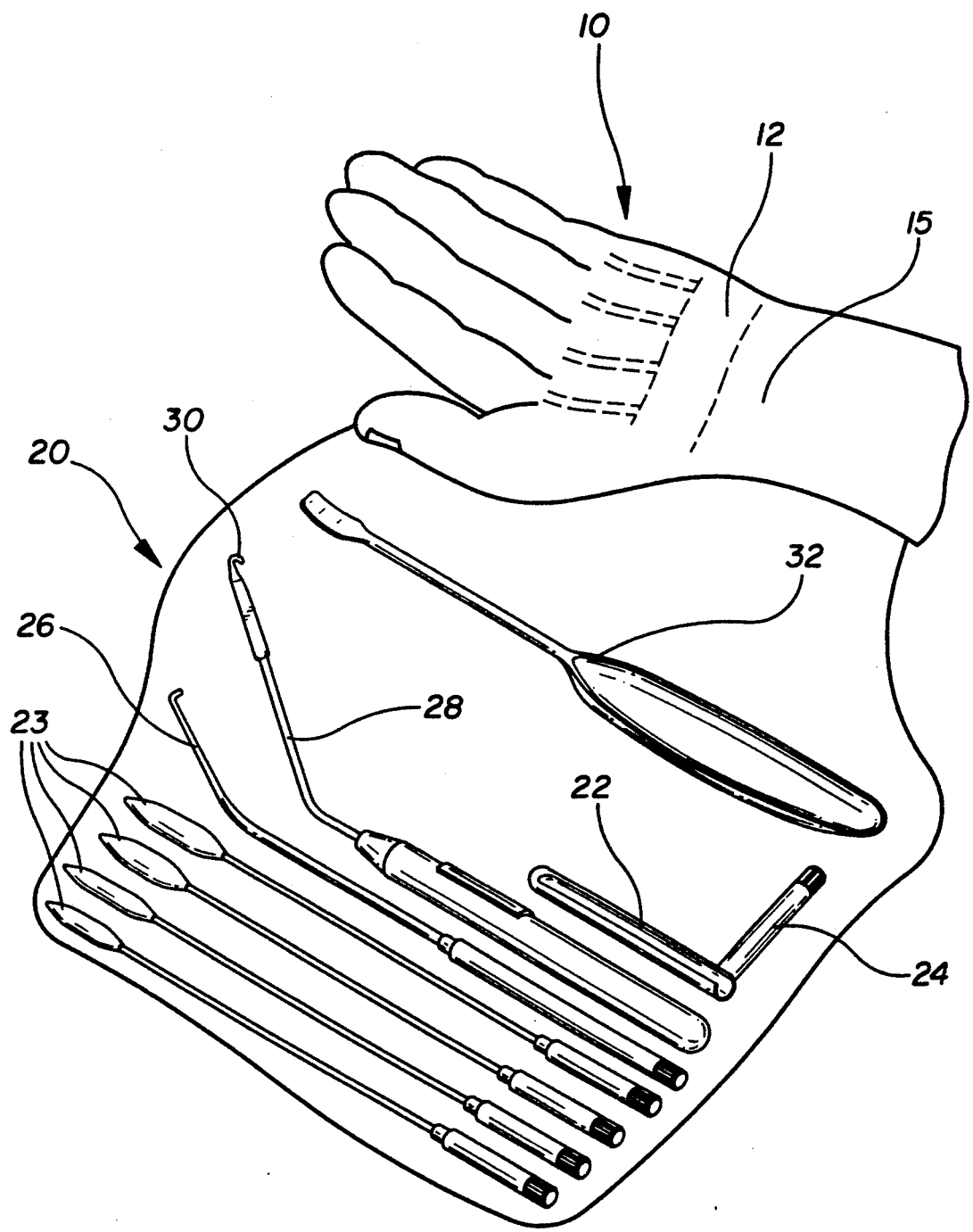
FIG. 2 is a perspective view of a carpal tunnel release kit of the present invention.

FIG. 2 shows a kit 20 in an embodiment of the present invention and a patient's hand 10. The dashed lines in the patient's hand 10 show structures which are ordinarily not visible since they are located deep below the patient's palmar skin.

The kit 20 includes a cannula 22 having a handle 24. Dilators 23 of various sizes are provided for opening the carpal tunnel prior to inserting the cannula 22 through a small incision 15 near the patient's wrist. An endoscope 40 is provided for viewing the transverse carpel ligament 12 from inside the cannula 22.

The dilators 23 are 4 millimeters (mm), 5 mm, 6 mm and 7 mm in diameter and are inserted sequentially into the carpal tunnel to create a pathway for the cannula 22. An elevator 32 is used to free the bursal tissue from the under surface of the transverse carpal ligament. A hooked probe 26 is used to locate the distal edge of the carpal ligament 22 prior to cutting. A knife 28 is provided for cutting the carpal ligament. For ease of manipulation both the probe and the knife have angled shafts, preferably approximately 45°. The knife 28 has a hooked blade 30 on one end so that the surgeon can cut the carpal ligament 22 in a distal to proximal manner.

Figure 3:
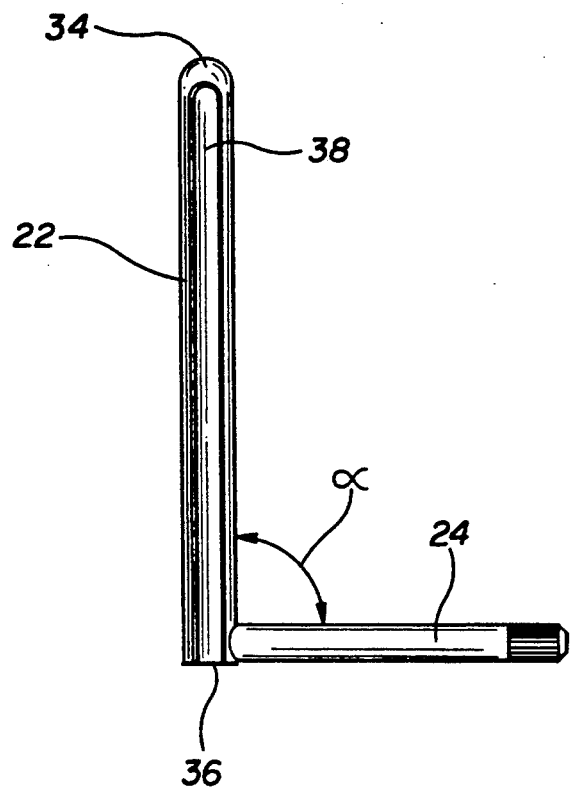
FIG. 3 is a top view of a cannula with a handle in a preferred embodiment of the present invention.

FIG. 3 shows a cannula 22 in a preferred embodiment of the present invention. The cannula 22 has a closed blunt end 34 and an open end 36. As shown, the cannula 22 also has a handle 24 attached to the cannula 22 near its open end 36. It is preferable for the angle $\alpha$ between the handle 24 and the cannula 22 to be approximately 90° so that the cannula can be held in a fixed position without interfering with the 45° angled tools which extend from the cannula's open end. The cannula 22 also has a slot 38 extending between its ends for allowing viewing and cutting of the patient's carpal ligament from inside the cannula 22.

Figure 4:
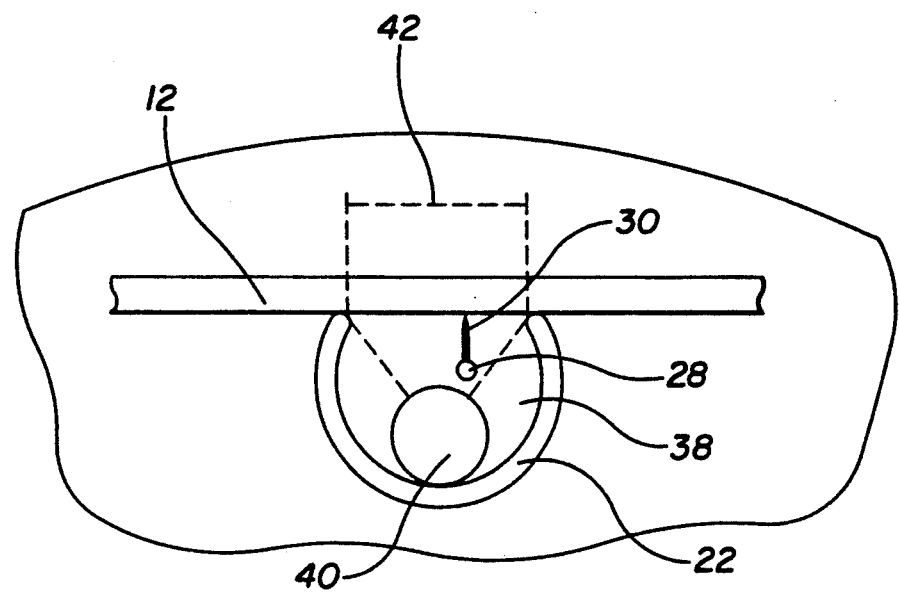
FIG. 4 is a sectional view of a cannula containing an endoscope and a knife in a preferred embodiment of the present invention.

FIG. 4 shows a cross-section of a cannula 22 during a carpal tunnel release procedure. The inner diameter of the slot 38 in the cannula 22 is large enough to contain the endoscope 40 and the knife 28 in order to protect surrounding tissue from accidental cutting or irritation. The width 42 of the slot 38 is sufficient to allow cutting of the ligament 12 by the hooked blade 30 while simultaneously viewing the procedure through the endoscope 40.

The cannula in a preferred embodiment of the present invention is a cylindrical tube of approximately 75 mm in length and 7 mm in diameter. The cannula has a 5 mm slot on its superior surface. One end of the cannula is closed and blunt. The other end of the cannula is open. There is a handle located near the open end and extending at a right angle from the cannula.

The cannula is preferably rigid enough so that it will not bend significantly during the surgery. The cannula should maintain a substantially straight path from the wrist incision to the distal edge of the transverse carpal ligament throughout the procedure. In a preferred embodiment of the invention, the cannula is made of an inert smooth metal which can be easily sterilized between uses. Other materials such as plastics or composites can be employed.

The preferred cannula described above is used to perform carpal tunnel release in conjunction with a 2.0 mm or 2.7 mm endoscope. The cannula is inserted into the wrist through a volar incision in the wrist and passed deep to the transverse carpal ligament. The endoscope is inserted into the cannula and the transverse carpal ligament is visualized through the slot. The ligament is then sectioned with the use of a hooked knife.

The method of the present invention for incising a carpal ligament in a patient who is experiencing carpal tunnel syndrome is initiated by first providing a cannula having a closed blunt end and an open end through which the knife and the endoscope may be inserted. The cannula has a slot extending between its ends for allowing viewing and cutting of the carpal ligament.

An incision, 1.2 cm in length, is made transversely in the skin on the volar aspect of the wrist 1 cm proximal to the volar flexion crease of the wrist and to the ulnar side of midline beginning adjacent to the palmaris longus tendon. The wound is deepened by blunt dissection until the volar retinaculum is exposed. The retinaculum is opened transversely. A 5 mm dilator is passed through the incision and directed into the carpal tunnel. Similarly, a 6 mm dilator and then a 7 mm dilator are consecutively passed into the carpal tunnel. An elevator is passed into the carpal tunnel and used to free the bursal tissue from the deep surface of the transverse carpel ligament. The cannula is inserted with the slot directed volar-ward against the deep surface of the ligament. The handle is used to maintain positional control of the cannula. A 2.0 mm or 2.7 mm endoscope is introduced into the cannula and the deep surface of the transverse carpal ligament visualized. A hooked probe is placed in the cannula adjacent to the endoscope, and under endoscopic visualization, the probe is used to identify the distal margin of the transverse carpal ligament. A hooked knife is then introduced and the ligament is cut from distal to proximal edges under endoscopic visualization. The hooked probe is used once again to probe the ligament to ensure that it has been sectioned in it's entirety. The cannula is removed and the wound is closed.

My claimed invention is not limited to the details of the preferred embodiments described above. I also claim all variations of my invention which are consistent in scope and spirit with the following claims.

I claim:

1. A method for incising a carpal ligament in a patient who is experiencing carpal tunnel syndrome comprising the steps of:
   providing a cannula having a closed blunt end and an open end through which a knife and an endoscope may be inserted, the cannula having a slot extending between its ends for allowing simultaneous viewing and cutting of the carpal ligament;
   making an incision near the patient's wrist;
   inserting the closed blunt end of the cannula through the incision and under the carpal ligament;
   inserting the endoscope into the open end of the cannula and viewing the carpal ligament through the cannula slot; and
   inserting a knife into the open end of the cannula and sectioning the ligament.

2. A method for incising a carpal ligament in a patient who is experiencing carpal tunnel syndrome, comprising:
   providing a cannula having a first end and an open end through which a knife and an endoscope are insertable, the cannula having a slot extending substantially between its end for allowing simultaneous viewing and cutting of a carpal ligament;
   making an incision near the patient's wrist;
   inserting the first end of the cannula through the incision and under the carpal ligament;
   inserting the endoscope into the open end of the cannula and viewing the carpal ligament through the cannula slot; and
   inserting, after the cannula is positioned under the carpal ligament, a knife into the open end of the cannula and sectioning the ligament.

3. The method of claim 2 further comprising guiding a probe alone the cannula and probing the distal edge of the carpal ligament prior to sectioning.

4. The method of claim 2 further comprising handling the cannula near its open end during the procedure by gripping a handle member which is rigidly and transversely attached to the cannula near its open end.

5. The method of claim 2 wherein the sectioning step is performed from the distal to proximal edges of the ligament.

6. A method for incising a carpal ligament in a patient who is experiencing carpal tunnel syndrome, comprising:
   providing a cannula having a first end and an open end through which a knife and an endoscope are insertable, the cannula having a slot extending substantially between its ends for allowing simultaneous viewing and cutting of a carpal ligament;
   making an incision proximal to the patient's wrist;
   inserting the first end of the cannula through the incision and under the carpal ligament;
   inserting the endoscope into the open end of the cannula and viewing the carpal ligament through the cannula slot;
   guiding a probe along the cannula and probing the distal edge of the carpal ligament prior to inserting the knife; and
   inserting, after the cannula is positioned under the carpal ligament, a knife into the open end of the cannula and sectioning the ligament.

7. The method of claim 6 further comprising handling the cannula near its open end during the procedure by gripping a handle member which is rigidly and transversely attached to the cannula near its open end.

8. The method of claim 7 wherein the sectioning step is performed from the distal to proximal edges of the ligament.

* * * * *